United States Patent

Rodriguez et al.

[11] Patent Number: 5,581,000
[45] Date of Patent: Dec. 3, 1996

[54] SULFONIC ACID-SUBSTITUTED ANTHRAHYDROQUINONE ALKYLAMMONIUM SALTS

[75] Inventors: Carmen L. Rodriguez, Exton; John G. Zajacek, Devon, both of Pa.

[73] Assignee: ARCO Chemical Technology, L.P., Greenville, Del.

[21] Appl. No.: 458,524

[22] Filed: Jun. 2, 1995

Related U.S. Application Data

[63] Continuation of Ser. No. 313,969, Sep. 28, 1994.
[51] Int. Cl.⁶ .............................. C09B 1/30; C07C 15/28
[52] U.S. Cl. .............................. 552/221; 552/234; 562/84
[58] Field of Search .................... 552/221, 234; 562/84

[56] References Cited

U.S. PATENT DOCUMENTS

| | | | |
|---|---|---|---|
| 3,311,453 | 3/1967 | Lusby | 423/588 |
| 3,923,966 | 12/1975 | Vaughan | 423/588 |
| 4,342,700 | 8/1982 | Sakai et al. | 260/370 |

FOREIGN PATENT DOCUMENTS

| | | |
|---|---|---|
| 673355 | 10/1963 | Canada . |
| 1256598 | 2/1961 | France . |
| 803121 | 10/1958 | United Kingdom . |
| 834264 | 5/1960 | United Kingdom . |

*Primary Examiner*—Joseph Conrad
*Attorney, Agent, or Firm*—Stephen D. Harper

[57] ABSTRACT

Hydrogen peroxide is produced by oxidizing alkylammonium salts of sulfonic acid-substituted anthrahydroquinones. As said salts are highly soluble in protic polar solvents such as water and lower aliphatic alcohols, the concentration of hydrogen peroxide in the reaction product thereby obtained may be advantageously high. The anthraquinone salt co-product generated by such oxidation may be readily converted in high yield back to the starting anthrahydroquinone salt by hydrogenation.

5 Claims, No Drawings

SULFONIC ACID-SUBSTITUTED ANTHRAHYDROQUINONE ALKYLAMMONIUM SALTS

This is a divisional of application Ser. No. 08/313,969, filed on Sep. 28, 1994 pending.

FIELD OF THE INVENTION

This invention pertains to methods of producing hydrogen peroxide wherein the alkylammonium salt of a sulfonic-acid substituted anthrahydroquinone is oxidized. Such salts have advantageously high solubilities in polar media such as water and methanol. The anthraquinone produced as a co-product may be hydrogenated to regenerate the anthrahydroquinone.

BACKGROUND OF THE INVENTION

For some time now, hydrogen peroxide has been commercially produced by the cyclic reduction and oxidation of anthraquinones, especially alkyl-substituted anthraquinones. The working solution in the commercial anthraquinone redox process is comprised of the anthraquinone, the corresponding anthrahydroquinone, and a water-immiscible organic solvent. One of the limiting factors in productivity is the amount of anthraquinone that can be retained in solution through the cyclic oxidation-reduction process. To increase the maximum concentration of anthraquinone usable in such a process, considerable effort has been devoted to varying the organic substituents on the anthraquinone and the type of organic solvent utilized. The use of water-soluble anthraquinones to avoid working material solubility limitations has also been proposed. For example, British Pat. No. 834,264 and French Pat. No. 1,256,598 teach that the alkali metal, alkaline earth metal, and ammonium salts of anthraquinone-2,7-disulfonic acid could be employed to manufacture hydrogen peroxide. Unfortunately, such salts have somewhat limited solubility in water (i.e., ≦300 g/L) and thus do not offer any substantial advantages over the conventional organic solvent-soluble anthraquinones.

SUMMARY OF THE INVENTION

We have now unexpectedly discovered that by forming the alkylammonium salt of a sulfonic acid-substituted anthraquinone, the solubility of such species in solvents such as water and methanol may be significantly enhanced. This surprising improvement in solubility makes possible the production of much higher hydrogen peroxide concentrations by means of an anthraquinone autoxidation process than had heretofore been feasible with the corresponding alkali metal, alkaline earth metal, or unsubstituted ammonium salts.

The invention provides a process for producing hydrogen peroxide comprising reacting a sulfonic acid-substituted anthrahydroquinone alkylammonium salt with molecular oxygen to form an oxidation reaction product comprised of hydrogen peroxide and a sulfonic acid-substituted anthraquinone alkylammonium salt.

DETAILED DESCRIPTION OF THE INVENTION

Sulfonic acid-substituted anthrahydroquinones suitable for use (in alkyl ammonium salt form) in the process of this invention include the class of organic substances containing both an anthrahydroquinone moiety and at least one sulfonic acid group (—SO$_3$H) pendent thereto. Such substances are well-known and are obtainable by direct sulfonation of the corresponding anthraquinone and subsequent hydrogenation. The sulfonic acid group(s) are preferably attached directly to the aromatic nuclei of the anthrahydroquinone, but may also be attached via intermediary groups such as methylene and the like. Preferably, at least two sulfonic acid groups per anthrahydroquinone molecule are present. Each anthrahydroquinone molecule may, for example, be substituted with two, three, four, or more sulfonic acid groups. The anthrahydroquinone may also bear other substituents such as hydrogen, alkyl, aryl, carboxyl, acyl, alkoxy, halide, and like groups, provided such substituents do not interfere with the desired oxidation-reduction reactions of the sulfonic acid-substituted anthrahydroquinone alkylammonium salt.

The sulfonic acid groups are converted into salt form wherein the cation is an alkylammonium species. For reasons which are not well understood, such salts have a much greater solubility in protic polar solvents such as water and methanol than the corresponding alkali metal, alkaline earth metal, or ammonium salt forms of such compounds. Preferably, the alkyl groups in such alkyl ammonium species are selected from lower alkyl groups (e.g., $C_1$–$C_6$), but most preferably are selected from methyl, ethyl, n-propyl, isopropyl, n-butyl, sec-butyl, iso-butyl, tert-butyl, or combinations thereof. For example, the alkylammonium cation may be tetramethylammonium, tetraethylammonium, or tetrabutylammonium. The alkylammonium cation may have from 1 to 4 alkyl groups substituted on the nitrogen atom.

The alkylammonium salts of sulfonic acid-substituted anthrahydroquinones preferably have the structure

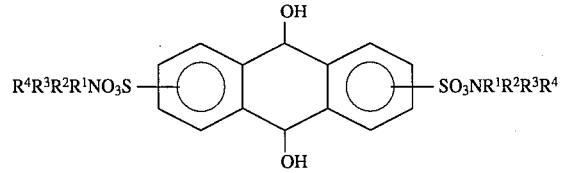

wherein $R^1$, $R^2$, $R^3$, $R^4$ are the same or different and are selected from the group consisting of hydrogen and $C_1$–$C_6$ alkyl, subject to the proviso that at least one of $R^1$, $R^2$, $R^3$ or $R^4$ is $C_1$–$C_6$ alkyl. Preferably, the total number of carbon atoms in $R^1$, $R^2$, $R^3$, and $R^4$ is from 4 to 16. Generally speaking, as the number of carbon atoms is increased, the solubility of the salt in alcohols such as methanol increases and the solubility of the salt in water decreases. The maximum concentration of a given salt in a liquid medium (and thus the maximum $H_2O_2$ concentration obtainable) may be readily optimized by adjusting the solvent system employed. The —SO$_3$NR$_4$ groups may be placed on any of the four available sites on each aromatic nucleus, with the other sites being preferably occupied by hydrogen (—H). Illustrative sulfonic acid-substituted anthrahydroquinones which may be used to prepare suitable alkylammonium salts include, but are not limited to, anthrahydroquinone-1,5-disulfonic acid, anthrahydroquinone-2,6-disulfonic acid, anthrahydroquinone-2-sulfonic acid, anthrahydroquinone-1,8-disulfonic acid, anthrahydroquinone-2,5-disulfonic acid, anthrahydroquinone-2,7-disulfonic acid, and the like. Mixtures of different sulfonic acid-substituted anthrahydroquinones may also be used to advantage.

The alkylammonium salt of the sulfonic acid-substituted anthrahydroquinone is preferably reacted with molecular oxygen in a liquid medium. The liquid medium is preferably selected such that the anthrahydroquinone and anthraquinone salts are fully dissolved at the reaction temperatures employed. The liquid medium preferably is comprised of a polar protic solvent. Examples of suitable polar protic solvents include water and $C_1$–$C_6$ aliphatic alcohols (e.g., methanol, isopropanol, tertiary butyl alcohol); mixtures of water and water-miscible organic solvents may also be advantageously employed. The solvent(s) selected should be inert under the conditions used in the oxidation and hydrogenation steps of the instant process. In one desirable embodiment of the invention, the volume of liquid medium utilized is minimized relative to the amount of anthrahydroquinone/anthraquinone but is still sufficient to fully dissolve or solubilize the anthrahydroquinone/anthraquinone. The concentration of hydrogen peroxide in the oxidation reaction product and thus the overall productivity of the process will thereby be maximized.

The reaction with molecular oxygen may be performed under conditions similar to those employed in conventional hydrogen peroxide processes involving an anthrahydroquinone species. Air, pure oxygen, or pure oxygen admixed or diluted with another gas such as nitrogen may serve as a source of molecular oxygen. Generally speaking, optimum reaction rates and selectivities may be achieved by operating at a temperature of from 0° C. to 100° C. and a partial oxygen pressure of from 5 to 200 psia. The oxidation is preferably carried out in the liquid phase, with the molecular oxygen preferably being sparged or otherwise introduced into the liquid medium containing the dissolved anthrahydroquinone salt. To minimize side reactions, such as the formation of oxidized anthraquinone by-products, the contact time of the salt is preferably limited (typically, less than about 30 minutes). The optimum contact time will be dependent upon the oxygen partial pressure, temperature, anthrahydroquinone salt reactivity, and other factors, but may be readily determined by routine experimentation. No catalyst is necessary to obtain the desired conversion of molecular oxygen to hydrogen peroxide.

The oxidation reaction product thereby obtained will typically comprise hydrogen peroxide, the alkylammonium salt of the sulfonic acid-substituted anthraquinone corresponding to the starting sulfonic acid-substituted anthrahydroquinone, as well as solvent and unreacted anthrahydroquinone salt. Hydrogen peroxide concentrations of least 5 weight percent or greater are attainable using the process of this invention.

The oxidation reaction product may be used directly as a source of hydrogen peroxide in any reaction where hydrogen peroxide is required, including, for example, the transition metal-catalyzed epoxidation of olefins and the like. Alternatively, the hydrogen peroxide could be separated from the sulfonic acid-substituted anthraquinone alkylammonium salt by a suitable method such as extraction or precipitation (through addition of calcium hydroxide to form a calcium peroxide, for example, as described in Canadian Pat. Nos. 673,355 and 715,979 and French Pat. No. 1,256,598).

The alkylammonium salt of the sulfonic acid-substituted anthraquinone generated as a co-product during the anthrahydroquinone oxidation step may be readily recycled by hydrogenation. Anthraquinone hydrogenation may be accomplished by reacting with molecular hydrogen ($H_2$) in the presence of a suitable hydrogenation catalyst. Such catalysts are well known in the art and include catalysts containing transition metals such as, for example, platinum, palladium, ruthenium, chromium (as in copper chromite, for example), nickel (as in Raney nickel, for example),and the like. Preferably, the hydrogenation catalyst is heterogeneous; the use of fixed bed hydrogenation reactions is especially advantageous. The transition metal may be supported on a suitable support such as alumina, carbon, or the like. Hydrogen partial pressures of from 0.5 to 200 atmospheres and temperatures of from 0° C. to 200° C. (more preferably, 20° C. to 120° C.) are generally sufficient to accomplish the desired degree of conversion of the anthraquinone to the corresponding anthrahydroquinone (typically, from 30 to 90%). The hydrogenation conditions should be selected so as to minimize over-reduction of the anthraquinone to species which will not form hydrogen peroxide upon reaction with molecular oxygen. The anthrahydraquinone obtained by hydrogenation is thereafter ready for a new cycle of oxidation and reduction.

EXAMPLES

Several tetraalkylammonium salts of anthraquinone-2,6-disulfonic acid were prepared starting with the commercially available disodium salt. For example, the tetrabutylammonium salt was obtained by dissolving the sodium salt into water and then adding 2 equivalents of tetrabutylammonium bromide. The resulting clear solution rapidly became turbid, yielding beige solids. The solids were collected by filtration, washed with water, and dried under vacuum to obtain the tetrabutylammonium salt.

The apparatus for the hydrogenation of the sulfonic-acid substituted anthraquinone salt consisted of a 50 ml Parr reactor equipped with a nitrogen inlet, hydrogen inlet, relief valve, overhead stirrer, fritted dip tube and thermocouple. Into the Parr reactor was introduced a mixture comprised of a heterogeneous hydrogenation catalyst (Raney nickel), solvent (varying ratios of methanol and water) and the tetrabutylammonium salt of anthraquinone-2,6-disulfonic acid. The mixture, once hydrogenated, was driven by use of nitrogen through the fritted dip tube (which retains the hydrogenation catalyst) into a separate apparatus wherein the hydrogenation product was oxidized. The oxidation apparatus consisted of a four neck 50 ml round bottom flask equipped with a condenser, nitrogen inlet, bubbler, air inlet, magnetic stirring bar, and stopper. The hydrogenation reaction product was oxidized in the presence of air, exhibiting a color change from caramel brown to pale yellow. The weight percent hydrogen peroxide in the resulting oxidation reaction product was then measured by iodometric titration.

The results obtained under varying conditions are shown in Table I. As may be seen, excellent selectivity to hydrogen peroxide was observed in many cases at moderately high conversions.

In another series of experiments, ruthenium on carbon (1% Ru) was evaluated as a hydrogenation catalyst in the process of the invention. The procedures used were similar to those described hereinabove. Good $H_2O_2$ selectivities were realized, as demonstrated in Table II.

To further demonstrate the advantages of the present invention, the relative solubilities of various salts of anthraquinone-2,6-disulfonic acid in water and methanol were measured. The observed solubilities are reported in Table III. The alkylammonium salts were generally found to be much more soluble in both water and methanol than the sodium and ammonium salts suggested by the prior art to be useful as reactants in hydrogen peroxide processes. Table IV lists the solubilities of certain alkylammonium salts usable in the process of this invention in water/methanol mixtures of varying proportions.

TABLE I

| Example | MeOH/H$_2$O | H$_2$ Pressure (psi) | Hydrogenation Time, hr. | Hydrogenation Temperature, °C. | Hydrogenation Catalyst, g | MMoles H$_2$ Consumed | MMoles H$_2$O$_2$ Produced | Conversion % | Selectivity % |
|---|---|---|---|---|---|---|---|---|---|
| 1 | 70/30 | 60 | 1 | 100 | 1.0 | 2.0 | 2.1 | 42 | 104 |
| 2 | 70/30 | 60 | 3.5 | 100 | 0.5 | 1.7 | 0.72 | 36 | 43 |
| 3 | 90/10 | 60 | 7.12 | 50 | 0.25 | 1.7 | 1.3 | 35 | 81 |
| 4 | 80/20 | 60 | 1.9 | 50 | 1.0 | 2.0 | 2.0 | 43 | 100 |
| 5 | 90/10 | 60 | 3 | 30 | 1.0 | 2.0 | 1.6 | 43 | 80 |
| 6 | 90/10 | 60 | 1.25 | 50 | 1.0 | 2.3 | 1.9 | 49 | 84 |
| 7 | 90/10 | 30 | 1.73 | 50 | 1.0 | 1.8 | 1.8 | 38 | 101 |

Conditions:
4.0 g anthraquinone-2,6-disulfonic acid, tetrabutyl ammonium salt
26.0 g solvent (MeOH/H$_2$O)

TABLE II

| Example # | Catalyst, g | Hydrogenation Time, Hr. | MMoles H$_2$ Consumed | MMoles H$_2$O$_2$ Produced | % Conversion | % Selectivity |
|---|---|---|---|---|---|---|
| 8  | 1.0[1]  | 20.6 | 0.38 | 0.17 | 8  | 45 |
| 9  | 1.0[2]  | 2.5  | 1.9  | 1.3  | 41 | 67 |
| 10 | 0.5[2]  | 3.5  | 1.7  | 1.3  | 35 | 75 |
| 11 | 0.25[2] | 7.0  | 1.7  | 0.99 | 37 | 57 |

[1]untreated
[2]prereduced
Conditions:
90/10 MeOH/H$_2$O solvent
4.0 g anthraquinone-2,6-disulfonic acid, tetrabutylammonium salt
30 psi H$_2$ pressure
50° C. (hydrogenation temperature)

TABLE III

| [Anthraquinone-2,6-disulfonate]$^{2-}$2X$^+$ X= | Solubility, g/L | |
|---|---|---|
|  | H$_2$O | MeOH |
| Na* | 10.24 | <0.022 |
| NH$_4$* | 14.37 | 0.047 |
| N(CH$_3$)$_4$ | 1426 | n.m. |
| N(CH$_2$CH$_3$)$_4$ | 1207 | 593 |
| N(n-butyl)$_4$ | n.m. | 851 |

*comparative example
n.m. = not measured

TABLE IV

| [Anthraquinone-2,6-disulfonate]$^{2-}$2X+ X= | Solubility, g/L (MeOH:H$_2$O) |
|---|---|
| N(CH$_2$CH$_3$)$_4$ | 1206 (10:90) |
| N(n-butyl)$_4$ | 200 (70:30) |
|  | 47.8 (45:55) |

We claim:

1. A sulfonic acid-substituted anthrahydroquinone alkylammonium salt having the structure:

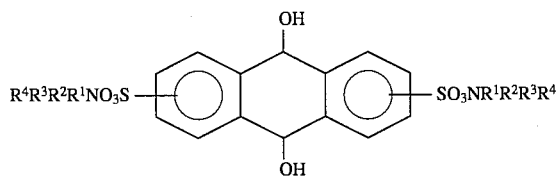

wherein R$^1$, R$^2$, R$^3$, and R$^4$ are the same or different and are selected from hydrogen and C$_1$–C$_6$ alkyl, subject to the proviso that each N is substituted with at least one C$_1$–C$_6$ alkyl.

2. The salt of claim 1 wherein R$^1$, R$^2$, R$^3$, R$^4$ are the same and are selected from the group consisting of methyl, ethyl, n-propyl, and n-butyl.

3. The salt of claim 1 wherein the —SO$_3$NR$^1$R$^2$R$^3$R$^4$ groups are in the 1,8, 2,5, 2,6, or 2,7 positions of the anthrahydroquinone.

4. The salt of claim 1 wherein R$^1$, R$^2$, R$^3$ and R$^4$ contain a total of from 4 to 16 carbon atoms.

5. A sulfonic acid substituted anthrahydroquinone alkylammonium salt having the structure

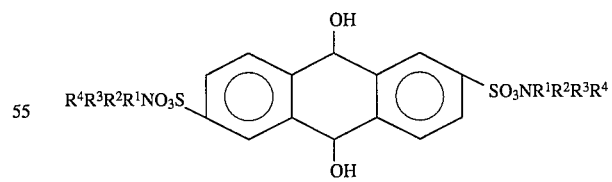

wherein R$^1$, R$^2$, R$^3$ and R$^4$ are the same and are selected from the group consisting of methyl, ethyl, n-propyl, and n-butyl.

* * * * *